United States Patent [19]

Bergin et al.

[11] 4,079,734

[45] Mar. 21, 1978

[54] TRACTION DEVICE FOR USE WITH A THOMAS SPLINT

[75] Inventors: Paul F. Bergin, Mishawaka; James L. Ritter, Akron, both of Ind.

[73] Assignee: Orthopedic Equipment Company, Bourbon, Ind.

[21] Appl. No.: 747,449

[22] Filed: Dec. 3, 1976

[51] Int. Cl.² ............................................. A61F 5/04
[52] U.S. Cl. ..................................... 128/84 C; 128/85
[58] Field of Search ................. 128/84 R, 84 A, 84 B, 128/84 C, 85, 71, 75; 242/96, 99, 74.1, 107.4 A

[56] References Cited

U.S. PATENT DOCUMENTS

| 238,887 | 3/1881 | Gorgas | 128/84 R |
|---|---|---|---|
| 965,648 | 7/1910 | Nace | 242/100 |
| 1,363,114 | 12/1920 | Hawley | 128/85 |
| 1,768,078 | 6/1930 | Krause et al. | 242/100 |
| 2,024,325 | 12/1935 | Allen | 128/85 |
| 2,516,925 | 8/1950 | Shaw | 128/87 |
| 2,821,978 | 2/1958 | Lindstrom | 128/85 |
| 3,086,519 | 4/1963 | Pari | 128/75 |
| 3,298,364 | 1/1967 | Radford | 128/75 |
| 3,477,428 | 11/1969 | Hare | 128/85 |
| 3,652,027 | 3/1972 | Wong | 242/96 |
| 3,741,496 | 6/1973 | Beller | 242/107.4 A |
| 3,906,942 | 9/1975 | Lumb | 128/84 C |

OTHER PUBLICATIONS

"Redi-Trac Traction Device" sold by Orthopedic Equipment Co. pamphlet, 10-75.

Rajowalt Fracture Equipment Pamphlet.

*Primary Examiner*—Robert W. Michell
*Assistant Examiner*—Michael H. Thaler
*Attorney, Agent, or Firm*—William D. Hall; Geoffrey R. Myers

[57] ABSTRACT

This invention relates to a traction device adapted to be slipped onto a lower-leg end of a Thomas splint and including resilient walls to provide a sufficient friction fit with said splint that the traction device will not fall off of the splint by its own weight but which may be readily manually removed from the splint. The traction device includes a socket which receives the splint and has two cylindrical housings molded integrally with the socket. The cylindrical housings form bearings and a shaft extends between the housings and receives a belt which is coiled upon the shaft when the shaft is rotated in one direction and uncoiled when the shaft is rotated in the other direction. The shaft is movable along its longitudinal axis. It is biased in one direction by a spring, in one of the housings, into a first operating position. In that position, a set of teeth on the inner end wall of the other housing engages a similar set of teeth on the inner end wall of a knob connected to the shaft, the teeth coacting to allow the shaft to rotate in only one direction to coil the belt upon the shaft. In a second operating position, which is attained by pulling the knob outwardly against the force of the spring, the shaft may rotate in either direction.

18 Claims, 10 Drawing Figures

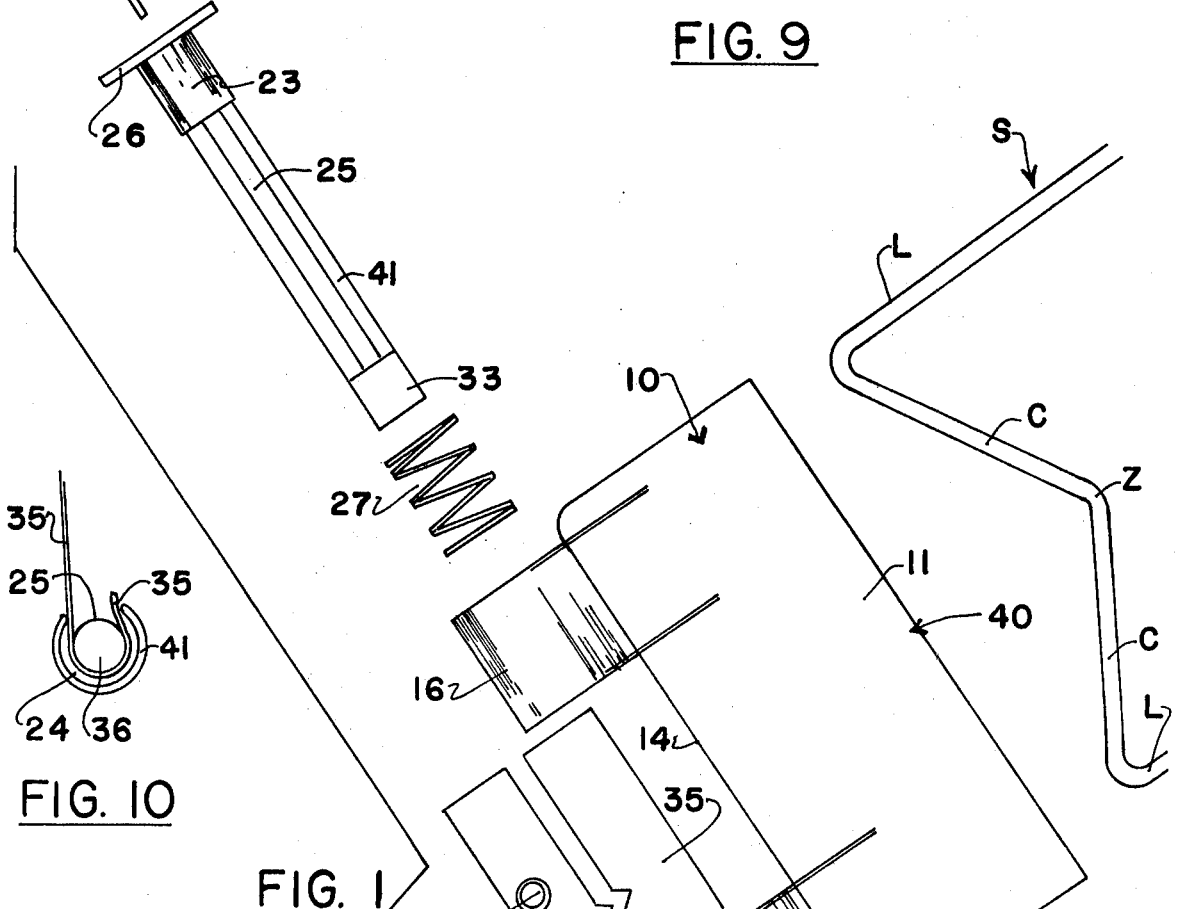

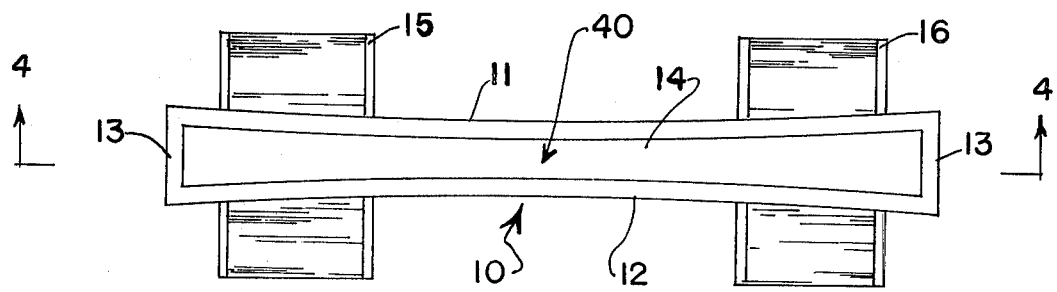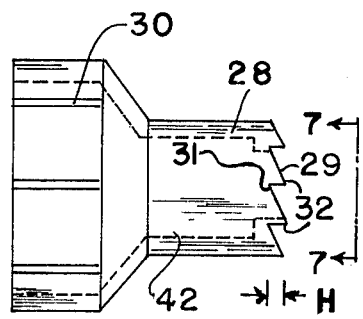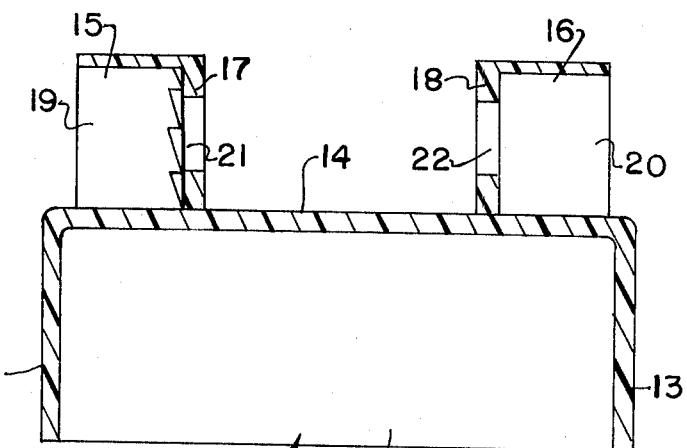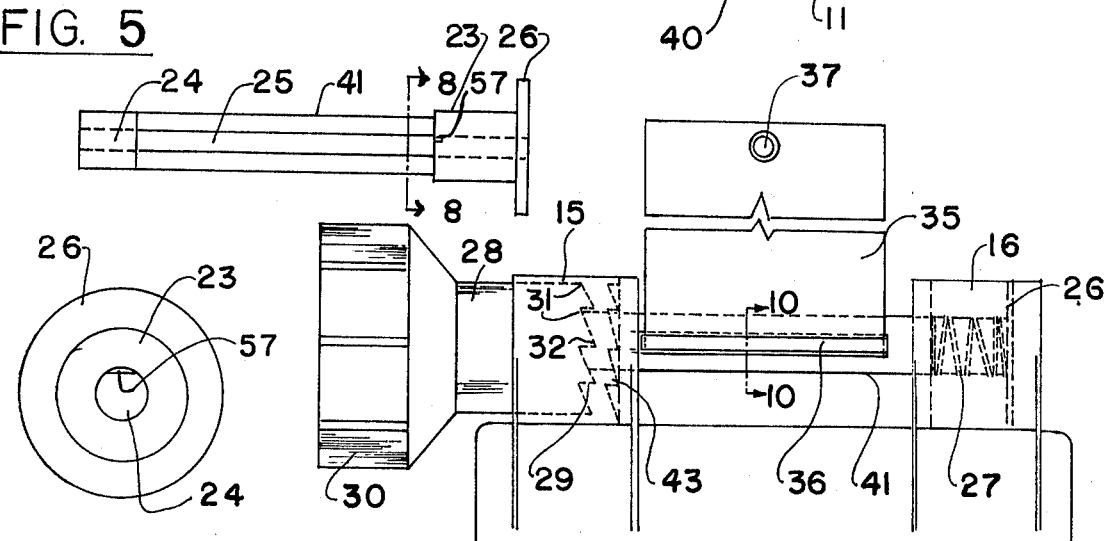

TRACTION DEVICE FOR USE WITH A THOMAS SPLINT

BACKGROUND OF THE INVENTION

There have been many prior art devices in which a traction device is attached at the end of a Thomas splint. See for example Shafer U.S. Pat. No. 819,607, entitled "Splint", issued May 1, 1906. In addition, there was a prior art traction device, in public use and on sale, employing two spaced channels which respectively engaged the two longitudinal members of the splint. There was a spring holding the traction device to the lower-leg cross arm of the splint. That prior art traction device had a ratchet, associated with a shaft, that allowed the shaft to rotate in only that angular direction in which the belt was coiled upon the shaft. A lever was operable to release the ratchet device so that the shaft could be rotated in either direction by the knob. A suitable knob was employed for rotating the shaft.

The prior art devices were expensive to manufacture and clumsy when in actual use. Moreover, the prior art traction devices were not capable of being easily attached to and/or removed from the splint.

The primary object of this invention is to provide a low cost traction device.

Another object of the invention is to provide a traction device that may be easily applied to and removed from the splint.

Still another object of the invention is the provision of a traction device in which all of the operations may be controlled by one knob, thus eliminating the ratchet release means of the prior art.

Yet another object of the invention is to provide a traction device of improved construction.

Still another object of the invention is to provide a traction device that is more reliable in operation than has heretofore been possible.

Other objects and advantages of the invention will become apparent as this description proceeds.

SUMMARY OF THE INVENTION

The invention employs a one-piece plastic socket element for receiving the lower-leg end of a Thomas splint. The socket member includes top and bottom walls which converge near the forward open end of the socket to thereby tend to hold the traction device onto the splint once the traction device has been inserted onto the splint. Two cylindrical housings are molded integrally with the socket both of which housings have end walls with holes therein to form bearings. A shaft passes through the bearings. A belt coils upon the shaft when the shaft rotates in one angular direction and uncoils when the shaft is rotated in the opposite angular direction. One end of the shaft terminates near the open end of the first cylindrical housing and there is a disc mounted on that end of the shaft. A helical coil spring tends to bias the disc and said shaft in an axial direction away from the bearings and into what is defined as a first operating position. There are teeth on the inner face of the second cylindrical housing and complementary teeth mounted on the inner face of the knob, connected to the other end of the shaft. The two sets of teeth mate with each other allowing the shaft to rotate in only that direction wherein the belt coils upon the shaft when the shaft is in said first operating position. The knob may be pulled in a direction away from said housing to move said shaft along its axis to a second operating position wherein the shaft may be rotated in either angular direction.

The shaft is tubular and has a slot from the outer wall of the shaft into the axial hole in the shaft. This slot is located between the two bearings and is longer than the width of the belt. The belt is attached to the shaft by folding the belt back on itself, projecting the folded portion into its slot, and inserting a pin in the hollow portion of the shaft to hold the folded portion of the belt in said slot and hole. The pin has a head, and there is a projection adjacent one end of the slot which limits the inward motion of the pin when the pin is moved along said axial hole.

BRIEF DESCRIPTION OF THE DRAWINGS

FIG. 1 is an exploded view of the various parts of the traction device together with an associated Thomas splint.

FIG. 2 is a front end view of the socket means and cylindrical bearings of the traction device.

FIG. 3 is an elevation view of the knob together with its associated series of teeth.

FIG. 4 is a cross sectional view taken along line 4—4 of FIG. 2.

FIG. 5 is a side view of the shaft.

FIG. 6 is a view of the traction device, fully assembled.

FIG. 7 is a front view of the teeth on the right end of the knob shown in FIG. 3.

FIG. 8 is a cross-sectional view of FIG. 5 taken along line 8—8.

FIG. 9 shows the traction device and splint assembled.

FIG. 10 is a cross-sectional view along line 10—10 of FIG. 6.

DETAILED DESCRIPTION OF THE DRAWINGS

In FIGS. 1 and 9, a conventional Thomas splint S has two longitudinal tubular members L having a hip engaging portion (not shown) and a lower-leg end portion characterized by the cross-arm C which has its two ends connected to the forward ends of members L and its central section Z. It is noted that the central section Z projects away from the lower-leg end of the splint S and toward the hip-end for a short distance in comparison to the length of the splint S. The traction device is adapted to be brought into engagement with a lower-leg end of splint S by inserting the forward end of the splint into the cavity of socket member 10. The socket member has rectangular top and bottom walls 11 and 12, two end walls 13 and a rear wall 14 connecting the top and bottom walls. The distance between top and bottom walls 11 and 12 is substantially the same as the thickness of the tubular members L, C, Z, of the splint S, except in the forward central portion of the cavity in socket means 10. The molded socket member 10 is composed of resilient plastic and the two walls 11 and 12 approach each other in the vicinity of the region 40. Thus, as the forward end of the splint S enters the socket member 10 the two longitudinal members L enter along the side walls 13 and as the splint S is further inserted into the socket means 10, the cross-arm C, which is inclined rearwardly toward zenith Z, causes the walls 11 and 12 to move away from each other in region 40 until the zenith Z has passed the region 40 at which time the reduced dimension between walls 11 and 12 at region 40 tends to pinch the cross-arm C in the region 40 of zenith Z, thus tending to hold the socket member 10 on the splint S.

The holding action is sufficiently strong that the socket member 10, and its associated traction device, will not fall off of the splint S, yet may be easily manually removed from the splint S. Molded integrally with the top wall 11, the bottom wall 12 and rear wall 14 are two cylindrical housings 15 and 16. Housing 15 has an end wall 17 and housing 16 has an end wall 18. The end walls 17 and 18 respectively have central openings 21 and 22 through which the shaft 41 passes. Since the openings 21 and 22 are only slightly larger in diameter than shaft 41, the end walls 17 and 18 constitute bearings for the shaft. At its right end, the shaft 41 includes a disc 26, the diameter of which is slightly less than the inner diameter of cylindrical bearing 16 and a helical coil spring 27 is located around the hub 23 and has one end in engagement with the disc 26 and the other end in engagement with wall 18. The helical coil spring 27 normally presses disc 26 clear to the open end of cylindrical housing 16. After the shaft 41 has been inserted through the coil spring then through the end walls 18 and 17 as shown in FIG. 6, the cylindrical hub 28 and gear teeth 29 are inserted in the open end cylindrical housing 15. Since the hub 28 has an internal axial hole 42 (FIG. 3) therethrough of the same diameter of the shaft 41, the shaft enters inside the hub 28 a short distance and is then heat sealed to the hub 28 by application of local heat. The heating tool may be inserted through the axial hole 42 in knob 30.

The teeth 29 at the rear end of hub 28 are shown in FIGS. 3, 6 and 7 and comprise a series of teeth with each tooth beginning at the base level 31 and projecting outwardly along a straight inclined path to a zenith 32 wherein the tooth surface sharply returns to the base level from whence the next inclined surface 31 of the next tooth begins. In other words, the teeth are of sawtooth shape. In actual practice, a typical tooth might be 5/16 inch wide (distance W), each inclined surface approximately 5/16 inch along (distance D), and each abrupt return surface ⅛ inch (distance H). It is noted that the aforesaid teeth are located between concentric circles 46 and 47 whose center falls upon the axis of the shaft. A similar set of teeth 43, with each tooth of the same dimension, and confined between concentric circles of the same diameters, as those for teeth 29, are molded on the inner side wall 17 of cylindrical housing 15. Two of the ten teeth shown in FIG. 7 are shaded to show the inclined surface.

The shaft is heat sealed to the knob 30 and hub 28, to so position the shaft 41 in the hub 28 that when there is no force applied to the knob 30, the spring 27 moves disc 26 to the open end of cylindrical housing 16 causing the teeth 29 to mesh completely with the teeth 43. In this "first" position of operation, the shaft can turn in only one angular direction since the abrupt return surface 32–31 of each tooth of the series 29 will be in engagement with a similar abrupt return surface of a tooth of the series 43, thus preventing rotation in said one angular direction. If, however, the knob is rotated in said one angular direction, the inclined surfaces 31–32 of the series of teeth 29 will ride up the similar inclined surfaces of the series of teeth 43. Hence, the knob may be rotated in said one angular direction for the purpose of turning the shaft 41 in that angular direction. If, however, the knob 30 is pulled to the left (FIG. 6) to compress spring 27, the series of teeth 29 will be out of engagement with the series 43 and the knob 30 together with the shaft 41 may be rotated in either angular direction. In order to apply traction to the patient, a conventional belt 35 having an eyelet 37 may be employed. The shaft 41 is a tube having a hole 24 extending from one end of the tube clear through to the other end including through the cylindrical hub 23 (around which the coil spring operates) and the disc 26. A slot 25 in the side wall of the shaft 41 extends from the outer surface of the shaft clear into the hole 24, and slot 25 is longer than the belt 35 is wide. In order to attach the belt 35 to the shaft 41, a limited portion of the belt, for example ½ inch thereof, near the free end thereof is folded back onto itself, and the folded portion inserted in slot 25 so that both the free end of the belt and the elongated belt portion are extending out of the slot 25 as shown in FIG. 10. Thereafter the pin 36 is inserted into the shaft 41 through the disc-end 26. The head of the pin is small enough to pass through the hole 24 in the shaft 41. However, since there is a projection 57 extending into the hole 24 at the right-hand end of the slot 25, the inward motion of the head of the pin 36 is stopped. Since the folded portion of the belt 35 extends around pin 36 and is clamped between the pin 36 and the inner wall of shaft 41, the belt is snugly held in place and will form a spiral coil upon the shaft when the shaft is rotated.

After the device has been assembled as aforesaid, it may be used as follows: If it is decided that traction should be applied to a leg located in or to be located in the splint S, the socket member 10 is inserted upon the lower-leg end of the splint S as previously described. If the belt from the shaft 41 is too long, its length may be reduced by turning the knob 30 (without pulling the knob outwardly) thus rotating the shaft in one angular direction and causing the belt to make a spiral coil upon the shaft 41. If, however, it is desired to release the belt so that it may move toward the leg of the patient, the knob 30 may be pulled in a direction away from cylindrical housing 15, thus moving disc 26 inwardly, compressing spring 27 and moving the sets of teeth 29 and 43 away from each other, whereupon the knob 30 may be rotated in either direction to provide whatever belt length is desired.

We claim to have invented:

1. A traction device for a leg splint having a hip end and lower leg end, said ends being connected by two spaced longitudinal members respectively, said splint including a cross arm connecting said longitudinal members at their lower-leg ends, comprising:

means for positioning the traction device in operative relation to the lower-leg end of the splint comprising a socket member having a front open end to enable a portion of the splint adjacent the lower-leg end to be slipped into the socket member a substantial distance, said socket member having resilient wall means comprising top and bottom walls generally spaced apart a distance slightly greater than the thickness of said portion of the splint, said top and bottom walls having closer spacing than said thickness of said portion of said splint in a region intermediate the ends of said front open end of said socket member thereby tending to hold said means on said splint when the splint is inserted into the socket member, a rotatable shaft, bearing means, supported by said socket member, for supporting siad rotatable shaft along an axis, a belt associated with said shaft which coils onto said shaft when the shaft is turned in one angular direction and which uncoils when the shaft turns in the other angular direction, and manually operable means for selecting either of two different modes of operation in one of which modes the shaft may rotate in only said one angular direction and in the other of which modes said shaft may rotate in either angular direction.

2. A traction device as defined in claim 1 in which, said cross arm has a central section which extends away from the lower-leg end of the splint and toward the hip end for a distance that is short compared to the length of the splint.

3. A traction device as defined in claim 2 in which the portion of said cross-arm that is closest to the hip-end of the splint is about mid-way between the longitudinal members of said splint, the closest relation of said top and bottom walls being at substantially the same location as said portion of said cross arm.

4. A traction device as defined in claim 3 in which the socket member and said bearing means comprise a one-piece molded plastic element.

5. A traction device as defined in claim 1 in which said manually operable means includes: (a) a knob connected rigidly to and rotatable with said shaft, (b) biasing means for biasing said shaft along its axis in one direction to one operating position to provide one of said modes of operation, (c) means for allowing said shaft to rotate in only said one angular direction when the manually operable means is in said one operating position, said knob being manually movable along its axis in a second direction against the force of said biasing means to another operating position where the knob and shaft may rotate in either angular direction to provide said second mode of operation.

6. A traction device as defined in claim 1 in which said shaft is tubular and defines an axial hole in the shaft and also defines an elongated slot in the wall of the shaft between said bearings to receive said belt and to expose the inner hole of the tube, and pin means movable along said hole to hold said belt to the shaft.

7. A traction device as defined in claim 1 in which said socket member includes two side walls and a rear wall each of which interconnect said top and bottom walls, and wherein said region intermediate the ends is midway of the ends, all of said walls together with said bearing means comprising a one-piece plastic element.

8. A traction device, for a leg splint that has two spaced longitudinal members terminating in a lower-leg end of the splint and a cross arm connecting said longitudinal members at their lower leg ends and having a central section which extends away from the lower-leg end of the splint, comprising socket means for receiving a limited portion of the splint adjacent its lower-leg end, said socket means defining a cavity and wall means comprising top and bottom walls respectively above and below the cavity, said top and bottom walls being spaced apart a distance slightly greater than the thickness of said portion of said splint, said top and bottom walls having closer spacing than said thickness of said portion of said splint in the region that said central section enters when the splint is inserted into the socket member, thereby tending to hold said socket means on said splint when said limited portion of said splint is received therein, a rotatable shaft, belt means, which coils upon said shaft when it is rotated in a first angular direction, for applying traction, bearing means mounted on said socket means for supporting said shaft on an axis, a knob on said shaft, biasing means for biasing the shaft along its axis to one operating position and permitting the shaft to be manually moved along its axis against the force of said biasing means to a second operation position, and shaft-direction control means for allowing the shaft to rotate in only one angular direction with the shaft is in said one operating position, while permitting the shaft to be rotated in either angular direction when the shaft is moved to its second operation position.

9. A traction device as defined in claim 8 in which said shaft-direction control means comprises first and second direction control members the first of which is mounted on said bearing means and the second of which is carried by said shaft, said members being biased into engagement by said biasing means and comprising means which when the members are in engagement with each other allows the shaft to rotate in only said one angular direction, said knob being movable against the force of said biasing means to move said members out of engagement with each other to allow the shaft to rotate in either angular direction.

10. A traction device as defined in claim 9, in which said bearing means comprises two spaced bearings, said shaft extending between said bearings and said belt being coiled on the shaft between said bearings, one of said bearings comprising a wall supported by said socket means, said wall having an opening through which said shaft passes, said first direction control member being mounted on that face of the last-named wall which is farthest from the other bearing.

11. A traction device as defined in claim 10 in which said first direction control member comprises a series of teeth extending between two concentric circles on said last-named face, said circles having their centerline along the axis of the shaft, each of said teeth comprising a tooth surface extending from said face along an inclined path which terminates in an abrupt return to said last-named face, said second direction control member including a series of teeth of the same shape as those of the first direction control member, which mate with the teeth on said last-named face when the shaft is in said first operating position, and which are removed from engagement with the teeth on said last-named face when said shaft is moved to said second operating position.

12. A traction device as defined in claim 8 in which said bearing means comprises spaced bearings supporting said shaft with the belt means being coiled on said shaft between said bearings, a cylindrical housing supported by said socket means; said housing having an end wall, constituting one of said bearings, at the end of the cylindrical housing closest to the other bearing; said end wall having an opening along its center line through which said shaft enters the cylinder, a disc carried in said cylinder by one end of said shaft, said biasing means comprising a helical spring in said cylinder one end of which spring bears against said end wall and the other end of which bears against said disc to bias said shaft along its axis to said one operating position, said knob being mounted on the end of said shaft opposite the end that carries said disc.

13. A traction device as defined in claim 12 having a second cylindrical housing having an end wall, constituting the other bearing, at that end of the housing closest to the first-named bearing; said last-named end wall having an opening along its center line through which said shaft enters, said shaft direction control means comprising a first member on the inner face of said last-named end wall and a second member mounted on said shaft, said first and second members being biased into engagement with each other when said spring biases said shaft into said first operating position and being out of engagement with each other when the shaft is moved into its second operating position by pulling said knob away from said bearing means, said last-named first and second members comprising means that allows said shaft to be rotated in only one direction when said members are in engagement with each other.

14. A traction device as defined in claim 13 in which said knob has an inner end facing said last-named end wall, said second member of said shaft-direction control means being integral with said knob and located on the inner end of said knob.

15. A traction device as defined in claim 14 in which said shaft is tubular and defines an axial hole in the shaft and also defines an elongated slot in the wall of the shaft between said bearings to receive said belt and to expose the inner hole of the tube, and pin means movable along said hole to hold said belt to the shaft.

16. A traction device, for a leg splint of the type having spaced longitudinal members terminating in a lower-leg end of the splint and a cross arm connecting said longitudinal members at their lower leg ends and having a central section which extends away from the lower-leg end of the splint, comprising socket means for engagement with a limited portion of the splint adjacent the lower-leg end, said socket means defining a cavity and wall means comprising top and bottom walls respectively above and below the cavity, said top and bottom walls being spaced apart a distance slightly greater than the thickness of said portion of said splint, said top and bottom walls having closer spacing than said thickness of said portion of said splint in the region that said central section enters when the splint is inserted into the socket means, thereby tending to hold said socket means on said splint when said limited portion of said splint is received therein, a tubular shaft having a hollow axial portion, a belt which is wide compared to its thickness, said tubular shaft having a slot in its side wall entering the hollow part of the shaft, said slot being at least as long as the width of said belt, pin means which is longer than the width of said belt insertable into the hollow portion of said shaft to hold a portion of the belt adjacent one end thereof in fixed position with reference to said shaft, and bearing means carried by said socket means for mounting said shaft for rotation.

17. A traction device as defined in claim 16 in which said pin means has a head at one end, and a projection extending into the hollow portion of said shaft at one end of said slot to limit the inward travel of said pin means.

18. A traction device, for a leg splint of the type that has two spaced longitudinal members terminating in a lower-leg end and also has a cross-arm at said lower-leg end that (a) connects the lower-leg ends of said longitudinal members and (b) has a portion between said longitudinal members which extends away from the lower-leg end of the splint for a distance which is short compared to the length of the splint, comprising a one piece molded plastic socket means and bearing means comprising top and bottom socket walls of generally rectangular shape, side walls connecting three of the four sides of said socket walls to thus define a cavity bounded by two closed lateral sides and a closed rear longitudinal side, said cavity having a front entrance to receive the lower-leg end of said splint, said top and bottom walls being of resilient material and converging in a region near the middle of said front entrance and otherwise farther apart than the thickness of the splint, the depth of the cavity rearward from said open end being at least as great as said distance, two cylindrical members projecting from at least one of said socket walls, each cylindrical member comprising a hollow cylinder having an end wall across that end of the cylinder which is closest to the other cylinder, each of said cylinders being open at its other end, said cylinders being on a common centerline which is generally perpendicular to the longitudinal members of the splint when the splint is inserted in said socket means, said end walls defining openings along their common center line to form bearings, the inner face of the end wall of the first of said cylindrical members having a series of teeth each tooth of which has a tooth surface which is inclined away from said face for a limited distance and then abruptly returns to said face, said converging walls tending to hold the cross-arm of said splint in the cavity once it is inserted therein, a tubular shaft extending through said openings in said end walls and also extending through the hollow second cylindrical member, said shaft having an axial hole therethrough and a slot extending from the outer surface of the shaft to said hole throughout an extended length of said shaft located between said end walls, a disc attached to the end of said shaft that is in the second cylindrical member, said disc being of smaller diameter than the inside diameter of the second cylindrical member, a helical spring in said second cylindrical bearing member, said spring being coiled around said shaft and having one end in engagement with the end wall of the first cylindrical member and the other end in engagement with said disc, a combined knob and toothed member in the first cylindrical member and connected to said shaft, said last-named toothed member having an end facing the inner face of the end wall of said first cylindrical housing and having a series of teeth each tooth of which has a tooth surface that is inclined away from the plane of the base of said teeth for a limited distance and then abruptly returns to said last-named plane, said first and second series of teeth mating with each other when said spring biases said shaft to bring the two series of teeth together thereby limiting rotation of said shaft to one direction, said spring having sufficient length of travel to permit the knob to be pulled against the force of said spring to move the second series of teeth from mating relation with the first series of teeth, to allow rotation of said shaft in either angular direction, a belt having a width less than the length of said slot, and a pin longer than the width of said belt and which may be slipped into the axial hole in said shaft to secure the belt to the shaft.

* * * * *